US010881299B2

(12) United States Patent
Wiest et al.

(10) Patent No.: US 10,881,299 B2
(45) Date of Patent: Jan. 5, 2021

(54) DEVICE AND METHOD FOR HYBRID OPTOACOUSTIC TOMOGRAPHY AND ULTRASONOGRAPHY

(71) Applicant: ITHERA MEDICAL GMBH, Munich (DE)

(72) Inventors: Christian Wiest, Munich (DE); Daniel Razansky, Munich (DE); Elena Mercep, Munich (DE); Pai-Chi Li, Taipei (TW); Geng-Shi Jeng, Tainan (TW)

(73) Assignee: Ithera Medical GmbH, Munich (DE)

( * ) Notice: Subject to any disclaimer, the term of this patent is extended or adjusted under 35 U.S.C. 154(b) by 1055 days.

(21) Appl. No.: 15/316,681

(22) PCT Filed: Jun. 10, 2015

(86) PCT No.: PCT/EP2015/062934
§ 371 (c)(1),
(2) Date: Dec. 6, 2016

(87) PCT Pub. No.: WO2015/189268
PCT Pub. Date: Dec. 17, 2015

(65) Prior Publication Data
US 2017/0164835 A1    Jun. 15, 2017

(30) Foreign Application Priority Data

Jun. 10, 2014 (EP) .................................. 14001989
Jun. 11, 2014 (EP) .................................. 14002003

(51) Int. Cl.
*A61B 5/00* (2006.01)
*A61B 8/00* (2006.01)
(Continued)

(52) U.S. Cl.
CPC .......... *A61B 5/0035* (2013.01); *A61B 5/0095* (2013.01); *A61B 5/725* (2013.01);
(Continued)

(58) Field of Classification Search
CPC ..... A61B 5/0035; A61B 5/725; A61B 5/0095; A61B 5/42; A61B 5/7253; A61B 5/7203;
(Continued)

(56) References Cited

U.S. PATENT DOCUMENTS

2010/0094134 A1* 4/2010 Zhu ...................... A61B 5/0073
                                                           600/473
2010/0249570 A1* 9/2010 Carson ................. A61B 5/0059
                                                           600/407

(Continued)

FOREIGN PATENT DOCUMENTS

JP        2012 239784 A      12/2012
WO    WO 2009/154298 A1    12/2009

OTHER PUBLICATIONS

International Search Report and Written Opinion prepared by the European Patent Office dated Dec. 16, 2015, for International Application No. PCT/EP2015/062934.
(Continued)

*Primary Examiner* — Peter Luong
(74) *Attorney, Agent, or Firm* — Sheridan Ross P.C.

(57) ABSTRACT

The invention relates to a device and an according method for hybrid optoacoustic and ultrasonographic imaging of an object (1), comprising an irradiation unit (2, 3) for irradiating the object (1) with electromagnetic radiation, in particular light, and a transducer unit (4) comprising a plurality of transducer elements (5), the transducer elements (5) being configured to emit ultrasound waves impinging on the object (1) and to detect ultrasound waves which are reflected and/or transmitted by the object (1) upon impinging on the object
(Continued)

Figure 1A:
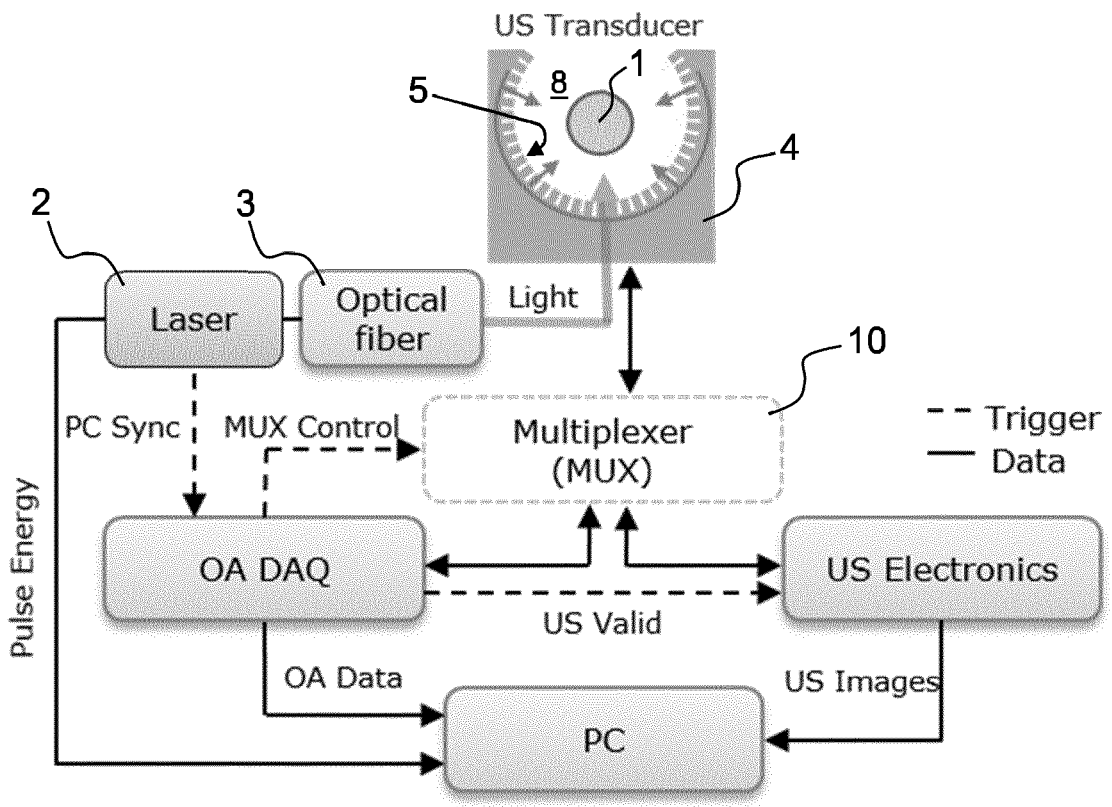

(1), and to detect ultrasound waves which are generated in the object (1) upon irradiation with electromagnetic radiation, wherein the transducer elements (1) are arranged along a curved line, in particular a concave line, or a curved surface, in particular a concave surface.

33 Claims, 6 Drawing Sheets

(51) Int. Cl.
    *A61B 8/15*     (2006.01)
    *A61B 8/08*     (2006.01)
    *G01S 15/89*     (2006.01)
    *A61B 8/14*     (2006.01)
    *G01N 21/17*     (2006.01)

(52) U.S. Cl.
    CPC ............... *A61B 8/14* (2013.01); *A61B 8/145* (2013.01); *A61B 8/15* (2013.01); *A61B 8/4444* (2013.01); *A61B 8/4455* (2013.01); *A61B 8/4494* (2013.01); *A61B 8/5207* (2013.01); *A61B 8/5246* (2013.01); *A61B 8/5253* (2013.01); *A61B 8/5261* (2013.01); *A61B 8/5269* (2013.01); *G01S 15/8927* (2013.01); *G01S 15/8929* (2013.01); *G01S 15/8952* (2013.01); *G01S 15/8993* (2013.01); *G01S 15/8995* (2013.01); *G01S 15/8997* (2013.01); *A61B 5/42* (2013.01); *A61B 5/7203* (2013.01); *A61B 5/7253* (2013.01); *A61B 2562/063* (2013.01); *G01N 2021/1706* (2013.01)

(58) Field of Classification Search
    CPC ....... A61B 8/14; A61B 8/4444; A61B 8/5246; A61B 8/145; A61B 8/4455; A61B 8/5207; A61B 8/5269; A61B 8/4494; A61B 8/15; A61B 8/5253; A61B 8/5261; A61B 2562/063; G01S 15/8952; G01S 15/8927; G01S 15/8929; G01S 15/8993; G01S 15/8995; G01S 15/8997; G01N 2021/1706

See application file for complete search history.

(56) References Cited

U.S. PATENT DOCUMENTS

| | | | | |
|---|---|---|---|---|
| 2011/0077526 A1* | 3/2011 | Zwirn | .................. | A61B 5/0095 600/459 |
| 2011/0306865 A1* | 12/2011 | Thornton | ............. | A61B 5/0059 600/407 |
| 2011/0319743 A1* | 12/2011 | Satoh | .................. | A61B 5/0095 600/407 |
| 2013/0217995 A1* | 8/2013 | Kruger | ................. | A61B 5/6835 600/407 |
| 2013/0276542 A1* | 10/2013 | Herzog | .................... | G01H 9/00 73/655 |
| 2013/0296684 A1 | 11/2013 | Miller et al. | | |
| 2014/0039317 A1* | 2/2014 | Sato | ........................ | A61B 8/54 600/443 |
| 2015/0208924 A1* | 7/2015 | Li | ........................ | A61B 5/0095 600/407 |

OTHER PUBLICATIONS

Mohammad A. Vase En et al: Hybrid optoacoustic and ultrasonic imaging system for detection of prostate malignancies, Proceedings of SPIE, vol. 6856, Feb. 7, 2008 (Feb. 7, 2008), p. 68560T.

A. Buehler et al: "Three-dimensional optoacoustic tomography at video rate", Optics Express, vol. 20, No. 20, Sep. 24, 2012 (Sep. 24, 2012), p. 22712.

Zalev Jason et al: "Opto-acoustic breast imaging with co-registered ultrasound", Progress in Biomedical Optics and Imaging, SPIE—International Society for Optical Engineering, Bellingham, WA, US, vol. 9038, Mar. 13, 2014 (Mar. 13, 2014), pp. 90381J-90381J.

Official Action for European Patent Application No. 19161869.3, dated Aug. 12, 2020, 4 pages.

* cited by examiner

DEVICE AND METHOD FOR HYBRID OPTOACOUSTIC TOMOGRAPHY AND ULTRASONOGRAPHY

CROSS REFERENCE TO RELATED APPLICATIONS

This application is a national stage application under 35 U.S.C. 371 and claims the benefit of PCT Application No. PCT/EP2015/062934 having an international filing date of Jun. 10, 2015, which designated the United States, which PCT application claimed the benefit of European Patent Application No. 14001989.4 filed Jun. 10, 2014 and European Patent Application No. 14002003.3 filed Jun. 11, 2014, the disclosures of each of which are incorporated herein by reference in their entirety.

The present invention relates to a device and a method for hybrid optoacoustic and ultrasonographic imaging of an object according to the independent claims.

Optoacoustic imaging is based on the photoacoustic effect, according to which ultrasonic waves are generated due to absorption of electromagnetic radiation by an object, e.g. a biological tissue, and a subsequent thermoplastic expansion of the object.

The invention is based on the problem to provide a device and a corresponding method allowing for improved hybrid optoacoustic and ultrasonographic imaging of an object, in particular for obtaining both optoacoustic and ultrasonographic images having high image quality and allowing for quantitative conclusions.

This problem is solved by the device and the method according to the independent claims. Preferred embodiments of the invention are part of the dependent claims.

According to an aspect of the invention, a device for hybrid optoacoustic and ultrasonographic imaging of an object comprises an irradiation unit for irradiating the object with electromagnetic radiation, in particular light, and a transducer unit comprising a plurality of transducer elements, the transducer elements being configured to emit ultrasound waves impinging on the object and to detect ultrasound waves which are reflected and/or transmitted by the object upon impinging on the object, and to detect ultrasound waves which are generated in the object upon irradiation with electromagnetic radiation. Preferably, the transducer elements are arranged along a curved line, in particular a concave line, or a curved surface, in particular a concave surface.

According to another aspect of the invention, a method for hybrid optoacoustic and ultrasonographic imaging of an object comprises the following steps: irradiating the object with electromagnetic radiation, in particular light, by means of an irradiation unit and detecting ultrasound waves, which are generated in the object upon irradiating the object with the electromagnetic radiation, by means of a plurality of transducer elements, and emitting ultrasound waves impinging on the object by means of the transducer elements and detecting ultrasound waves, which are reflected and/or transmitted by the object upon impinging on the object, by means of the transducer elements. Preferably, two-dimensional hybrid optoacoustic and ultrasound imaging is performed by cylindrically focusing the transducer elements onto a common (two-dimensional) imaging plane and arranging the transducers along a curved line, in particular a concave line, in order to effectively collect two-dimensional tomographic information around the imaged object.

The invention allows for a reconstruction of both optoacoustic (OA) images and ultrasound (US) images in two or three dimensions having high image quality and allowing for quantitative conclusions.

According to another preferred aspect of the invention, hybrid pulse-echo ultrasonographic and optoacoustic imaging is performed in three dimensions, preferably by using a concave two-dimensional array of transducer elements by means of which ultrasound waves reflected by the object upon impinging on the object and/or generated in the object upon irradiation with electromagnetic radiation are detected. In this case, the transducer elements are optimally arranged along a curved surface, in particular a concave surface, in order to effectively collect three-dimensional tomographic information around the imaged object.

According to yet another preferred aspect of the invention, instead of or in addition to pulse-echo ultrasonographic imaging, where ultrasound images are obtained by detecting ultrasound waves which are reflected by the object, ultrasonographic imaging is performed in a transmission mode, wherein ultrasound images are obtained by detecting ultrasound waves which are transmitted through the object. Preferably, one or more first transducer elements are configured and/or controlled only to emit ultrasound waves impinging on the object, while a plurality of second transducer elements are configured and/or controlled to detect ultrasound waves which are transmitted through the object upon impinging on the object. Preferably, at least the second transducer elements are focused onto a common imaging plane and arranged along a curved line, in particular a concave line, in order to effectively collect two-dimensional tomographic information in transmission mode. Preferably, the angular coverage of the concave array of second transducer elements is close to 360°. Surprisingly, good imaging results can also be achieved when providing an angular coverage below 360°, i.e. between 270° and 330°, preferably of approximately 270°. Advantageously, ultrasonographic imaging in transmission mode, in distinction to pulse-echo ultrasonography, delivers images with contrasts that reflect local variation of speed of sound and sound attenuation.

Accordingly, the device and method according to preferred aspects of the invention allow for three different types of imaging, i.e. optoacoustic tomography and/or pulse-echo ultrasound tomography and/or transmission-mode ultrasound tomography.

Preferably, the transducer elements are arranged along an arc-shaped, bow-shaped or arcuate line and/or surface. Alternatively or additionally, the transducer elements are arranged on a cylindrically shaped or spherically shaped surface. Preferably, the transducer elements are arranged in a curved, in particular concave, one-dimensional or two-dimensional array.

Preferably, the transducer elements are arranged along a concave line or concave surface, respectively, to cover an angular range of between 120° and 300° around the object, which is preferably located in the center of curvature of the concave line or concave surface, respectively.

According to further preferred embodiments at least one of the following applies: the curved line or curved surface, respectively, exhibiting a radius of curvature being in the range between 20 mm and 60 mm; the transducer elements being configured to emit ultrasound waves in a range of frequencies around a central frequency; the central frequency of the transducer elements being between 2 and 8 MHz; the number of the transducer elements is at least 50, preferably at least 100; the arrangement of the transducer elements exhibiting a pitch size in the range of between 0.3 mm and 1 mm, preferably of approximately 0.3 mm; the transducer elements exhibiting a pitch size in the range of between 0.1 mm and 3 mm. Preferably, the term "pitch" relates to a distance between the centers of neighboring transducer elements, i.e. transducer elements which are bordering each other.

Preferably, the transducer elements cover a major part of the curved line or curved surface, respectively. Alternatively or additionally, the transducer elements are arranged adjacently to each other.

According to another preferred embodiment, the device comprises a cavity in which a coupling medium, in particular water, is accommodated, the cavity comprising a curved cavity surface corresponding to the curved surface along which the transducer elements are arranged.

According to yet another preferred embodiment, the device comprises a multiplexer unit configured to switch the transducer unit between different operation modes, wherein in a first mode (receive-only mode) ultrasound waves generated in the object upon irradiation with electromagnetic radiation are received by the transducer elements, and/or in a second mode (transmit-and-receive mode) ultrasound waves are emitted by the transducer elements and ultrasound waves reflected and/or transmitted by the object are received by the transducer elements, and/or in a third mode (mixed mode) ultrasound waves generated in the object upon irradiation with electromagnetic radiation are received by a first subset of the transducer elements and ultrasound waves are emitted by a second subset of the transducer elements and ultrasound waves reflected and/or transmitted by the object are received by the second subset of the transducer elements, wherein the first subset of transducer elements is different from the second subset of transducer elements. Preferably, the multiplexer unit is programmable to enable temporally multiplexed acquisition in the different operation modes, wherein in the receive-only mode, corresponding to the optoacoustic tomography mode, ultrasound waves generated in the object upon irradiation with electromagnetic radiation are received by the transducer elements, in the transmit-and-receive mode, corresponding to a reflection ultrasound tomography mode, ultrasound waves are emitted by the transducer elements and ultrasound waves reflected and/or transmitted by the object are received by the transducer elements, and in the mixed mode, corresponding to an interleaved optoacoustic and reflection ultrasound tomography mode, a first subset of available transducer channels, i.e. transducer elements, operate in the receive-only mode and a second subset of the available transducer channels operate in the transmit-and-receive mode. The advantage of interleaved acquisition is a higher achievable frame rates due to flexibility to select lower number of transducer channels for ultrasound acquisition keeping all channels active for optoacoustic acquisition and vice versa, rather than using the same set of channels in both modes.

Preferably, the irradiation unit comprises a light emitting element and/or a light guide, in particular a fiber bundle. Preferably, the device comprises a control unit for controlling the irradiation unit and the transducer unit such that the irradiation unit irradiates the object with pulsed electromagnetic radiation.

According to yet another preferred embodiment, the device comprises a processing unit configured to reconstruct at least one two-dimensional and/or three-dimensional image of the object based on ultrasound waves, which are reflected and/or transmitted by the object upon impinging on the object and/or generated in the object upon irradiation of the object with electromagnetic radiation, and detected by the transducer elements arranged along a concave line or a concave surface. Preferably, the transducer elements are arranged in a concave, in particular spherically shaped, two-dimensional array.

Preferably, the multiplexing control unit comprises two different acquisition electronics having different input impedances. Preferably, an optoacoustic acquisition electronics has a high input impedance which is beneficial for optoacoustic imaging, while the input impedance of an ultrasound acquisition electronics is matched to the ultrasound array dedicated for the ultrasound tomography mode. This enables efficient coupling of the excitation pulse in ultrasound mode, while still not hampering the sensitive detection abilities in optoacoustic imaging mode.

It is, moreover, preferred that the device is configured for programmable segmentation of ultrasound acquisitions, where a finite group of transducer channels or elements transmitting ultrasound waves and detecting the reflected ultrasound signals in a defined order constitutes a single data acquisition (DAQ). This can be used in combination with a trigger signal (e.g. created by a pulsed light source for optoacoustic imaging) which communicates the start of an optoacoustic acquisition. After a specified delay an individual or multiple ultrasound DAQs can be executed depending on the optoacoustic frame rate, where an image can only be reconstructed after all ultrasound DAQs are complete. This allows the acquisition of multiple optoacoustic images while one reflection-mode ultrasound image is acquired by segmenting the ultrasound acquisition, hence enabling increased optoacoustic frame rate while retaining ultrasound frame rate. This "laser-triggered" behavior contributes to optimizing the stability of the laser by enabling a controlled energy build up and bundled release as compared to triggering the laser from outside electronics.

Preferably, to further accelerate execution of single image formation a pipeline processing is executed, wherein a set of processing steps, such as demodulation, dynamic apodization in receive and synthetic aperture beamforming, are executed after a first DAQ is completed using data from the respective channels, while execution of the second DAQ starts without waiting for the preceding set of signal processing instructions to be completed. Spatial compounding and logarithmic compression are conducted after all DAQs are complete. If N DAQs are required and each takes the time T to be completed, then when employing the pipeline processing, instead of sequential processing, the formation of one image takes (N−1)·T less time, since all stages of data acquisition are executed in parallel to signal processing stages.

An emitted acoustic waves propagates in a diverging manner leading to a constructive interference at points where the path length for an ultrasound pulse between opposite edges of the emitting transducer element differs by one or multiple wavelengths, known as side lobes or grating lobes if same applies to the distance between two transducer elements. The energy in these subsidiary beams is considerably less than that of the main lobe and decreases radially away from the main beam, where the angle between the main beam and the side lobe axes is directly proportional to the transmitted wavelength and inversely proportional to the effective width of the aperture.

According to yet another preferred embodiment, exciting subsequent transducer elements with varying frequency (e.g. 5, 2.5, 2.5, 2.5, 5 MHz, etc.), also referred to as frequency mixing, results in grating lobe reduction. Because the location of grating lobe is dependent on the center frequency, the idea behind grating lobe reduction is to use different frequencies for each transmit/receive event in a way of interleaving (i.e., 5 MHz for the transmission with the first element, followed by 2.5 MHz for transmission with the second element etc). Hence, the location for each grating lobe caused by different frequencies differs, and with coherent summation, the location of grating lobe for different frequencies can be suppressed. Preferably, the frequency mixing sequence and number of cycles are optimized with respect to the grating lobe level, and results in lower side lobe level and narrow main lobe compared to the excitation with constant frequency.

According to yet another preferred embodiment, the device comprises a control unit configured to control the transducer elements to sequentially emit ultrasound pulses impinging on the object and to simultaneously detect ultrasound waves which are reflected and/or transmitted by the object upon impinging on the object, whereby ultrasound pulses are sequentially transmitted from each of the transducer elements, while the ultrasound pulses reflected and/or transmitted by the object are received by all of the transducer elements or by a pre-defined number or a subset of transducer elements. In this embodiment, a so-called synthetic aperture (SA) beamforming is applied to generate an image of the object from a specific view angle spanned by a section of the total imaging aperture, in following also referred to as a sub-aperture, wherein a sub-aperture preferably comprises a plurality of transducer elements arranged along a curved line or a curved surface. Details regarding synthetic aperture beamforming can be found, e.g., in Karaman M, Li P-C, O'Donnell M. Synthetic aperture imaging for small scale systems. IEEE Trans Ultrason Ferroelectr Freq Control 1995; 42:429-42, which is incorporated by reference herewith.

A particular advantage of applying the SA technique to the concave transducer array over conventional beamforming with fixed transmit focus is that it allows for two-way dynamic focusing for each image point regardless of the reconstructed image format. Conventional ultrasound beamforming methods often use line-by-line scan, wherein an image is composed by a multiple of scan lines, wherein for each line a fixed range is focused when transmitting and dynamic focusing in receive is done along the range. Applying this method to concave arrays would lead to a degradation of image quality when the image points lie away from the transmit focus since the single transmit beam direction is not aligned with the pre-defined scan line due to arrangement of the transducer elements along the concave line. In distinction to this, applying the SA technique to concave transducer arrays combines a design optimized for optoacoustic imaging with an improved, more flexible image formation in ultrasound imaging.

Preferably, the control unit is configured to control the transducer elements such that only transducer elements of a subset of the transducer elements sequentially emit ultrasound pulses impinging on the object and simultaneously detect ultrasound waves which are reflected and/or transmitted by the object upon impinging on the object, whereby ultrasound pulses are sequentially transmitted from each of the transducer elements of the subset of the transducer elements, while the ultrasound pulses reflected and/or transmitted by the object are received by all of the transducer elements of the subset of the transducer elements. In this embodiment, which is also referred to as sparse SA beamforming or sparse synthetic transmit aperture imaging, instead of using all of the transducer elements of the transducer unit, only a subset of the transmit and receive elements is used for US image acquisition. In this way, the imaging frame rate of the data acquisition can be set or configured in a simple and reliable way via the number and/or a selection of transducer elements which are configured and/or controlled to both transmit an ultrasound wave and receive the reflected signals.

According to yet another preferred embodiment, the device comprises a control unit configured to control transducer elements of a first set of the transducer elements to sequentially emit ultrasound pulses impinging on the object and transducer elements of a second set of the transducer elements to simultaneously detect ultrasound waves which are reflected and/or transmitted by the object upon impinging on the object, wherein a distance between the transducer elements of the first set of transducer elements is different from a distance between the transducer elements of the second set of transducer elements, whereby ultrasound pulses are sequentially transmitted from each of the transducer elements of the first set of transducer elements, while the ultrasound pulses reflected and/or transmitted by the object are received by all of the transducer elements of the second set of transducer elements. Preferably, the transducer elements of the first set of transducer elements are constituted by every second transducer element of the transducer unit and the transducer elements of the second set of transducer elements are constituted by every third transducer element of the transducer unit. Alternatively, the transducer elements of the first set of transducer elements are constituted by every third transducer element of the transducer elements, and the transducer elements of the second set of transducer elements are constituted by every fourth transducer element of the transducer elements. In this embodiment, a so-called Vernier array for sparse SA beamforming is used in order to further increase imaging frame rate while maintaining the image quality. A Vernier array or Vernier pattern of the transducer elements exhibits different spacings between active ultrasound emitting or transmitting transducer elements, on the one hand, and ultrasound receiving transducer elements, on the other hand. If non-sparse effective aperture has a spacing of exactly p between adjacent elements, then a sparse aperture has a spacing of kp, where k is integer. For example, the different spacings exhibit a 2:3 relation, wherein transmit array is spaced by kp=2p, so every $3^{rd}$ transducer element (first set of transducer elements) is used for transmitting ultrasound waves, and receive array is spaced by kp=3p, so every $4^{th}$ transducer element (second set of transducer elements) is used for receiving ultrasound waves. In this case, the effective two-way aperture, that represents the convolution between transmit and receive apertures (areas spanned by transmit and receive elements, respectively), is fully sampled while the separate transmit and receive apertures are sparsely sampled.

According to yet another preferred embodiment, the device comprises a processing unit configured to perform spatial compounding processing, wherein the same region of the object is scanned by transducer elements, which are arranged along the curved line or curved surface, from multiple view angles and wherein the resulting beamformed images obtained from sub-apertures, which are given by subsets of the transducer elements, are incoherently summed up to form a final composite image. Preferably, the synthetic aperture (SA) beamforming described above is combined with the spatial compounding (SC) processing, whereby (1) the optimal sub-aperture size of a large-coverage angle concave transducer array is determined and (2) a plurality of sub-images formed by the sub-apertures is compounded to a final image. Preferably, the sub-apertures overlap partially. Preferably, the number of beamformed images for spatial compounding across different view angles, which relates to the overlap between adjacent sub-apertures, the size of individual sub-apertures and the total angular span of the transducer array, determines the level of speckle reduction and image smoothing. Preferably, the overlap between the sub-apertures constitutes between 0.5 to 0.9 times, preferably approximately 0.75 times, the individual sub-aperture size. The size of an individual sub-aperture is preferably not larger than 180° and can be optimized, for example, by means of numerical simulations using metrics of main lobe width and peak-to-side-lobe ratio. Preferably, the size of the sub-apertures is between 60° and 180°, preferably between 110° and 160°.

According to the aforementioned embodiments, synthetic aperture beamforming has been adapted to be applicable to a concave transducer array. While using the entire aperture of a curved array for beamforming would result in poor performance, employing sub-apertures, preferably of optimized size as explained above, results in improved image quality.

According to yet another preferred embodiment, the transducer elements comprise first transducer elements being designed for emitting ultrasound waves impinging on the object and detecting ultrasound waves which are reflected and/or transmitted by the object upon impinging on the object, the first transducer elements having a first size and a first pitch, and second transducer elements being designed for detecting ultrasound waves which are generated in the object upon irradiation with electromagnetic radiation, the second transducer elements having a second size and a second pitch, wherein the first size of the first transducer elements is smaller than the second size of the second transducer elements and/or the first pitch of the first transducer elements is smaller than the second pitch of the second transducer elements.

Preferably, the first transducer elements being further designed for detecting, apart from ultrasound waves which are reflected and/or transmitted by the object, ultrasound waves which are generated in the object upon irradiation with electromagnetic radiation.

Preferably, the first transducer elements are arranged along a curved line or curved surface to cover a first angular range around the object, and the second transducer elements are arranged along a curved line or curved surface to cover a second angular range around the object, wherein the second angular range is larger than the first angular range.

Preferably, the first transducer elements are arranged along a curved line or curved surface to cover a first angular range around the object, and the first transducer elements and the second transducer elements are arranged along a curved line or curved surface to cover a third angular range around the object, wherein the third angular range is larger than the first angular range.

Advantageously, for optoacoustic imaging the angular coverage of the transducer elements, which detect ultrasonic waves generated upon illuminating the object with light, is enlarged or maximized, while a small pitch of the first transducer elements is beneficial for active ultrasound imaging. Therefore, the transducer unit preferably has transducer elements with different size and/or pitch, wherein ultrasound imaging is performed with a subset of smaller first transducer elements, whilst a high angular coverage is realized including larger second transducer elements. Optoacoustic imaging can be performed with the larger second transducer elements (covering a second angular range around the object) only. Alternatively, optoacoustic imaging can be performed with all transducer elements, i.e. with the smaller first transducer elements and the larger second transducer elements (covering together a third angular range around the object), whereas ultrasound imaging is performed by the smaller transducer elements (covering a first angular range around the object) only.

According to yet another preferred embodiment, the first transducer elements being part of at least one first transducer element array having at least one first focus, and the second transducer elements being part of at least one second transducer element array having at least one second focus, wherein the at least one first focus does not coincide with the at least one second focus. In this embodiment, different foci of the first and second transducer elements are provided, wherein the position of the foci of the first and second transducer elements may be optimized for ultrasound or optoacoustic imaging, respectively. While in the prior art transducer arrays are typically formed on a single piece of piezocomposite, the transducer unit preferably comprises separate first and second transducer element arrays which are formed from multiple pieces and can have, depending e.g. on the shape and/or orientation, different foci. In this way, for example, the first focus of the first transducer elements can be focused deeper into the object than one or more second foci of the second transducer elements to enable deeper ultrasound imaging, which is less obstructed by light absorption in deep tissues as compared to optoacoustic imaging.

Preferably, the ultrasound image rate is increased by progressively combining individually acquired images to a preliminary image using the DAQs of the previous complete sequence of images. This allows the creation of an updated image for each DAQ. This increases effective image rate, but does not change the amount of motion that impacts an individual image, because it still consists of data from the same amount of data acquisitions, as an image is always composed of the N last acquisitions. Maximizing the distance between subsequent sub-apertures (hence shuffling the order of acquisitions) can help to better cope with large influences of motion, since all image areas get updated more frequently.

According to another preferred embodiment, acquisition time frames are compressed by combining sparse SA with a time domain overlap in excitation and detection, while retaining sufficient spatial separation between two overlapping acquisitions in different channels. In a specific manifestation, this means excitation using a first detector element and subsequent detection using all receive channels in the sub-aperture, where a second emission on another detector element on a distinct sub-aperture is initiated with a short delay to the first emission, but during the receive timeframe of the first sub-aperture. The length of the delay and the available angular coverage (determines the possible distance between emissions) determines the amount of interference of the emitted pulse with scattered previous pulses emitted from other sensors. Given the known distance and speed of sound between elements direct detection of the excitation pulse can be avoided, however inference of the waves in the coupling medium will decrease SNR, which to some extent can be counter-balanced by an increased effective acquisition rate. The achievable speed-up here is determined by the spatial extents of the detector array, where larger arrays allow more distance between concurrent emissions, limiting the interference. This approach is also referred to as compressed sensing scheme for synthetic aperture (CSSA) by which an overlap in time domain between transmission and detection is ensured, while scarcity in spatial domain is ensured by means of a sufficient interval between the first and the second sub-apertures.

It is, furthermore, preferred to perform a model-based reconstruction for transmission ultrasound tomography. Preferably, for rendering maps of local variations of speed of sound and/or acoustic attenuation coefficient, an iterative reconstruction algorithm based on an expectation maximization (EM) algorithm is used. Details regarding the EM algorithm can be found, e.g., in Dempster A P, Laird N M, Rubin D B. Maximum likelihood from incomplete data via the EM algorithm. J R Stat Soc Ser B 1977; 39:1-38, which is incorporated by reference herewith. The forward imaging model represents an overdetermined system of linear equations where each equation corresponds to one combination of transmit-receive transducers associated with transmitted wave. E.g. for an i-th pair of the sending-receiving transducer elements along the propagation path:

$$g_i = \Sigma_j H_{ij} f_j, \quad (1)$$

where $g_i$ denotes the measured signal, $H_{ij}$ is the ultrasound system response matrix containing the sound traveling distances in the intersected pixels for each sending-receiving pair, and $f_j$ the local speed of sound or attenuation coefficients of all pixels located within circumference of transducer array. If the estimate of the 2D image of the sound velocity or attenuation coefficient at n iteration is denoted as $\hat{f}_j^n$, then the solution reads:

$$\hat{f}_j^{n+1} = \frac{\hat{f}_j^n}{\sum_i H_{ij}} \sum_i H_{ij} \frac{g_i}{\sum_j H_{ij} \hat{f}_j^n}. \quad (2)$$

Additionally, edge-preserving regularization, e.g. total variation or total generalized variation regularization can be applied to the sound speed or attenuation map reconstruction. Details regarding total variation can be found, e.g., in Panin V Y, Zeng G L, Gullberg G T. Total variation regulated EM algorithm [SPECT reconstruction]. IEEE Trans Nucl Sci 1999; 46:2202-10, which is incorporated by reference herewith. Details regarding total generalized variation can be found, e.g., in Knoll F, Bredies K, Pock T, Stollberger R. Second order total generalized variation (TGV) for MRI. Magn Reson Med Off J Soc Magn Reson Med Soc Magn Reson Med 2011; 65:480-91, which is incorporated by reference herewith.

Preferably, in order to obtain a more accurate estimate of the time-of-flight (TOF), each transmit-receive signal pair is deconvolved with the corresponding system frequency response which is obtained from a reference measurement in water. A moving average filter (e.g. of size 3) in the time dimension is applied to three successive TOF estimates. This can eliminate the variation of TOF estimation caused by noise.

Preferably, the device comprises an image enhancement unit which is configured to improve OA/US hybrid images by using the dual contrast of the images, wherein quality and accuracy of multi-spectral optoacoustic tomography (MSOT) images is enhanced using anatomical features and reflectivity contrast delivered by reflection mode ultrasound computed tomography (RUCT) and information on heterogeneous sound velocity and acoustic attenuation (AA) distribution in tissue delivered by transmission mode ultrasound computed tomography (TUCT). Vice versa, to improve quality, accuracy and specificity of the RUCT/TUCT images anatomical features and optical contrast delivered by the MSOT imaging is used.

Preferably, OA/US hybrid images are manually or automatically segmented into at least two regions based on the dal contrast of the images.

Preferably, the automated segmentation of hybrid images into at least two regions based on dual contrast of the images comprises the following steps:
 a. image pre-processing using filtering in the frequency domain and/or an anisotropic diffusion filter for noise reduction and edge sharpening,
 b. starting contours initialization:
    determined by means of manual segmentation,
    determined automatically by Canny or Sobel edge detection and morphological processing of the edge map→calculating centroids for connected components of the binary edge map→centroids clustering into finite number of groups based on computation of pairwise distances between centroids→computing minimal bounding circles for each centroid cluster,
 c. automated region growing-shrinking, wherein for each pixel for each of the initial contour selecting the inner (inside the contour) and outer (outside the contour) neighboring pixels, adding excluding the pixels from the segmented region based on the homogeneity criterion,
 d. updating the borders of the segmented region,
 e. repeating steps c to d until there are no pixels to add or exclude from the region.

Changes in density and velocity of sound between adjacent tissues, jointly referred to as an acoustic impedance mismatch, make the outer skin layer and boundaries of internal organs clearly visible with RUCT. Inherent co-registration between ultrasound and optoacoustic images facilitates cropping an optoacoustic image outside the object boundaries, reducing the border artifact in multispectral optoacoustic images. Motion of the sample can also more easily be seen using the RUCT images (deformation/motion of the border of the object) and hence help the multispectral processing by sorting out or realigning motion compensated multispectral images. Therefore, according to an advantageous aspect of the invention, by the device accurate cropping of an optoacoustic image outside the object boundaries is facilitated, reducing the border artifact in multispectral optoacoustic (MSOT) images, as well as reflection ultrasound images are used for optimizing the MSOT experiment workflow by enabling detection of improper membrane coupling, air bubbles, hair.

According to another advantageous aspect of the invention, the analysis of object borders clearly visible in RUCT images is done to elucidate the motion of the object through deformation of the borders in order to determine the live status of a living sample as well as to perform motion correction.

Speed of sound is a critical reconstruction parameter for achieving optimal resolution and contrast in optoacoustic tomographic images. The optoacoustic reconstruction procedure, as explained in Deán-Ben X L, Ntziachristos V, Razansky D. Effects of small variations of speed of sound in optoacoustic tomographic imaging. Med Phys 2014; 41:073301, which is incorporated by reference herewith, requires an a priori knowledge of the speed of sound distribution within the imaged sample. Conventional optoacoustic reconstruction algorithms are based on the assumption of a homogeneous speed of sound equal to the average value of speed of sound in the imaging sample and coupling medium. Preferably, to account for speed of sound changes between different organs and structures, an automated calibration of multiple speed of sound values is implemented comprising the following steps:
  a. creating a multi-level mask which encodes each segmented region as a unique integer and is generated manually or automatically according to the elucidations set forth above,
  b. initializing calibration objective function that takes as input the set of speed of sound values for multiple regions and returns the quantitative measure of sharpness of the resulting optoacoustic image,
  c. assigning each i-th region an initial speed of sound value $c^i_0$ based on TUCT measurement of speed of sound and acoustic attenuation. Alternatively, initialization of the starting speed of sound value can be conducted assuming homogeneous initial speed of sound distribution,
  d. running the solver for the unknown speed of sound values that minimizes the objective function,
  e. reconstructing an optoacoustic image using the map of fitted speed of sound values for each segmented region.

Preferably, 2D maps of speed of sound distribution in the object obtained by the aid of transmission mode ultrasound tomography can be directly used as an input to model-based tomographic optoacoustic reconstruction to account for spatial speed-of-sound variations in tissue.

According to yet another embodiment, the regularization term in the inverse TUCT problem for unknown map of speed of sound values is derived from the optoacoustic image, specifically, at each reconstruction iteration step the focus metric is calculated for the optoacoustic image reconstructed with the respective estimate of the speed of sound map and is used to penalize speed of sound maps largely deviating from the correct values. An additional penalty term can be introduced for a more accurate estimation of speed of sound distribution, namely the quantitative measure of sharpness of the optoacoustic image. Even the slight deviation of the assumed speed of sound from the correct value leads to characteristic artifacts in reconstructed optoacoustic images that manifest in form of degraded contrast and distorted boundaries of the object. Any of the focus metrics disclosed in Mandal S, Nasonova E, Deán-Ben X L, Razansky D. Optimal self-calibration of tomographic reconstruction parameters in whole-body small animal optoacoustic imaging. Photoacoustics 2014; 2:128-36, which is incorporated by reference herewith, can be used as a regularization term in solving the inverse problem set forth in Eq. (2) above for an unknown 2D image of the speed of sound:

$$\hat{f}=\arg\min_f \|g-Hf\|^2+\lambda\|R(f)\|^2, \quad (3)$$

where g denotes the measured data for all detector pairs, H is the ultrasound system response matrix containing the sound traveling distances in the intersected pixels for each sending-receiving pair, f is local speed of sound in all pixels located within circumference of transducer array, R is the sharpness of the optoacoustic image reconstructed with previous $\hat{f}$ estimate of the speed of sound map.

In optoacoustic imaging the absorbed laser energy density represents the product of the absorption coefficient and the light fluence distribution. Enabling quantitative optoacoustic imaging requires a corrective measure, which accounts for heterogeneous light fluence. The fluence is related to the absorption coefficient distribution $\mu_a$ and the reduced scattering coefficient distribution $\mu_s'$ and, therefore, can be modeled for different tissue types. The fluence correction scheme is based on the absorption maps derived from the segmented ultrasound image (assuming a structural difference in tissue will likely impose changes in optical properties) and preferably includes the following steps:
  a. creating a multi-level mask which encodes each segmented region of the ultrasound image as an unique integer,
  b. assigning each region an initial estimate of absorption $\mu_a^0$ and scattering coefficients $\mu_s^{0'}$,
  c. calculating the fluence using a model of the propagation of light,
  d. calculating the objective function as root mean square error between the measured and calculated absorbed energy maps,
  e. running the solver for the unknown absorption pa and scattering coefficients $\mu_s$ of each of the segmented regions that minimizes the objective function using a gradient-based minimization scheme.

Modelling of light transport in biological tissue in step c. is preferably done with the diffusion approximation to the radiative transfer equation, or with the δ-Eddington approximation to the radiative transfer equation, as disclosed in T. Saratoon et al., 3D quantitative photoacoustic tomography using the δ-Eddington approximation, Proceedings of SPIE—The International Society for Optical Engineering, 03/2013, which is incorporated by reference herewith.

In summary, implementation of hybrid imaging using both optoacoustics and pulse-echo ultrasound brings together the important advantages and complementary contrasts of both methods. Yet, the fundamentally different physical contrast mechanisms of the two modalities may also impose significant differences in the optimal tomographic data acquisition and image formation strategies. Real-time acquisition of optoacoustic data by a mere addition of an illumination source to the widespread ultrasound linear arrays may lead to significant limited-view artefacts in optoacoustic reconstructions and overall loss of image quality and quantification abilities. Vice versa, unsatisfactory ultrasound image quality would be achieved with tomographic arrays which are solely tailored for optimal optoacoustic image acquisition. Therefore, according to aspects of the present invention, curved transducer array designs and algorithmic strategies are proposed in order to overcome the key limitations of hybrid real-time image acquisition with significant improvements showcased in both optoacoustic and pulse-echo ultrasound images acquired from both tissue-mimicking phantoms and mice.

ALTERNATIVE ASPECTS OF THE INVENTION

Although aspects and preferred embodiments of the invention set forth herein preferably relate to a device and method for hybrid optoacoustic and ultrasonographic imaging of an object, alternative aspects of the invention also relate to a device and a corresponding method for optoacoustic imaging only as well as to a device and corresponding method for ultrasonographic imaging only.

Therefore, a first alternative aspect of the invention relates to a device for optoacoustic imaging of an object, comprising an irradiation unit configured to irradiate the object with electromagnetic radiation, in particular light, and a transducer unit comprising a plurality of transducer elements, the transducer elements being configured to detect ultrasound waves which are generated in the object in response to the irradiation with electromagnetic radiation, wherein the transducer elements are preferably arranged along a curved line, in particular a concave line, or a curved surface, in particular a concave surface.

Preferred embodiments of the first alternative aspect of the invention are set forth in the dependent claims, the above description as well as the following description with reference to the figures, wherein each of the embodiments relating to aspects of optoacoustic image acquisition and reconstruction may although mentioned in connection with a hybrid OA/US imaging device and method also be applied to and combined with the above device and corresponding method for "pure" optoacoustic imaging of an object.

Moreover, a second alternative aspect of the invention relates to a device for ultrasonographic imaging of an object, comprising a transducer unit comprising a plurality of transducer elements, the transducer elements being configured to detect ultrasound waves which are reflected and/or transmitted by the object, wherein the transducer elements are preferably arranged along a curved line, in particular a concave line, or a curved surface, in particular a concave surface. Preferably, the transducer elements are further configured to emit ultrasound waves impinging on the object.

Preferred embodiments of the second alternative aspect of the invention are set forth in the dependent claims, the above description as well as the following description with reference to the figures, wherein each of the embodiments relating to aspects of ultrasonographic image acquisition and reconstruction may-although-mentioned in connection with a hybrid OA/US imaging device and method also be applied to and combined with the above device and corresponding method for "pure" ultrasonographic imaging of an object.

Figure 2:
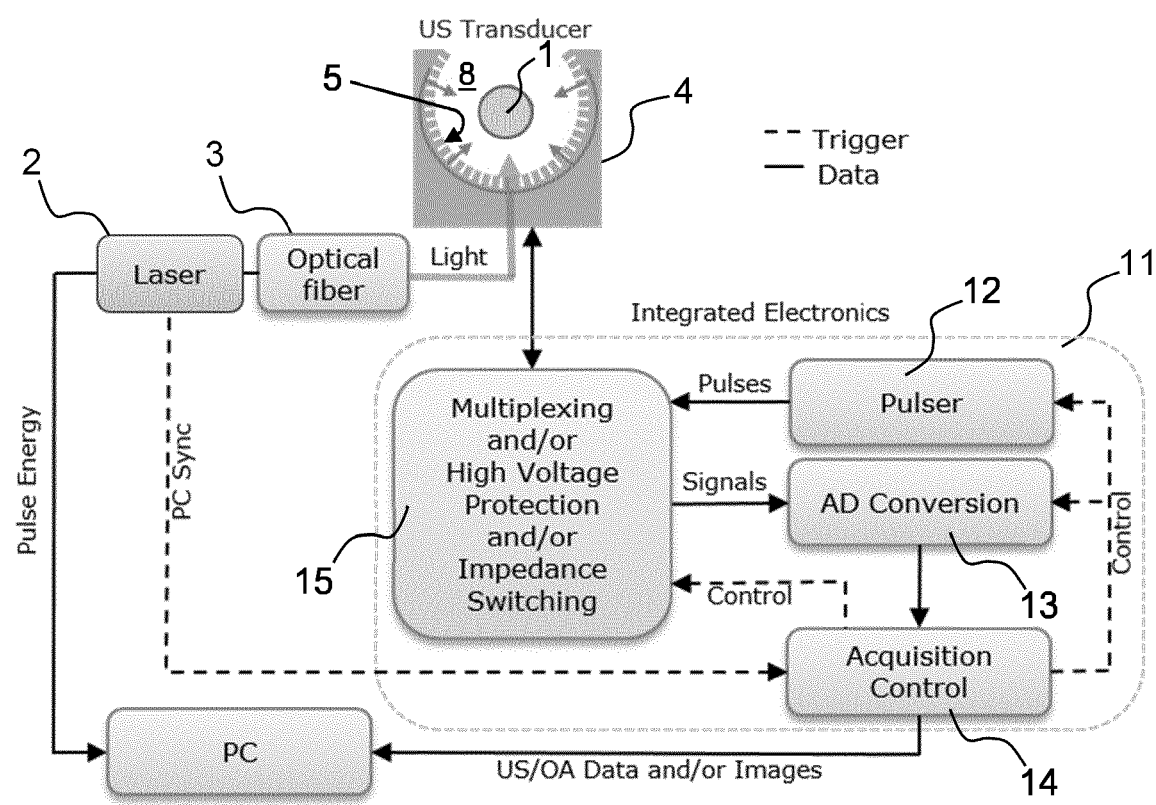
Figure 3:
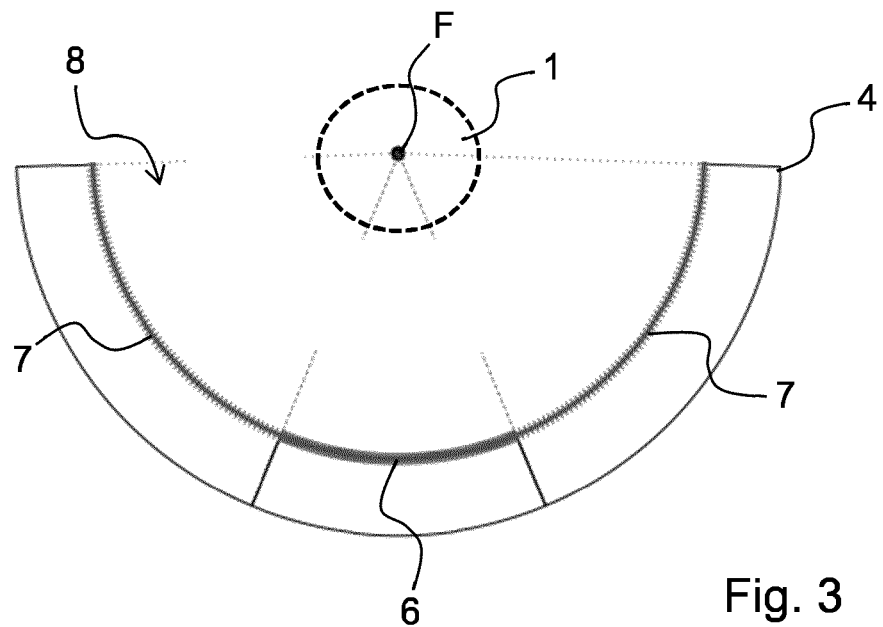
Figure 4:
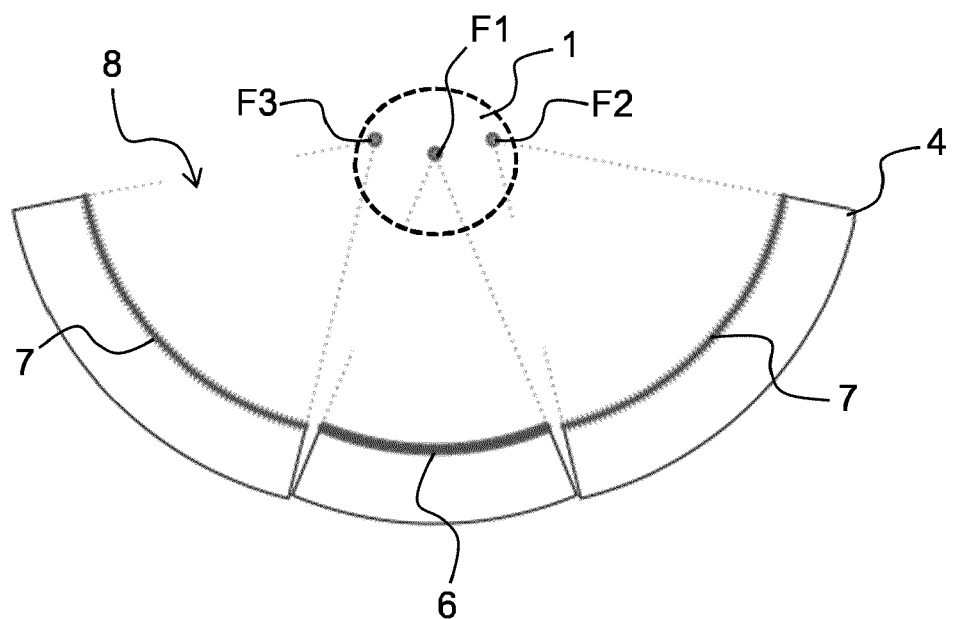
Figure 5:
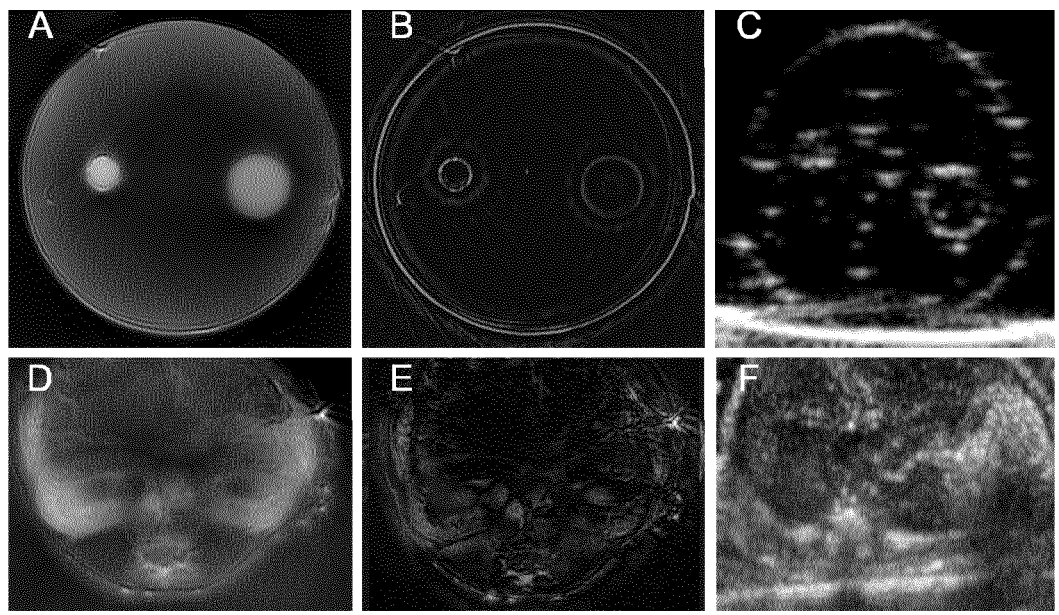
Figure 6:
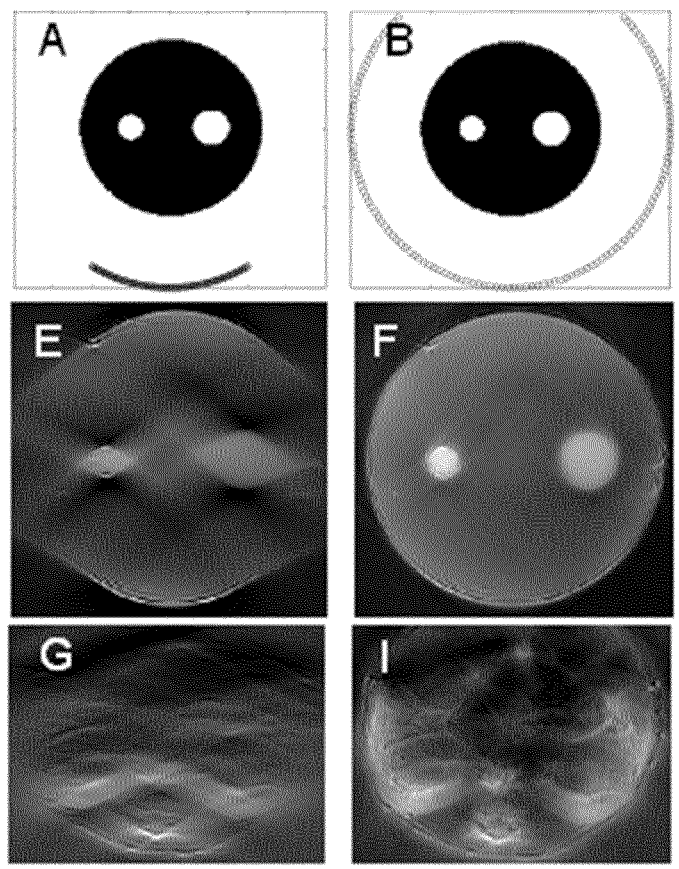
Figure 7:
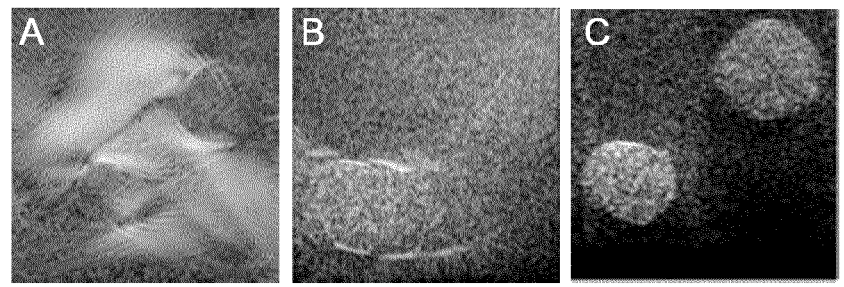
Figure 8:
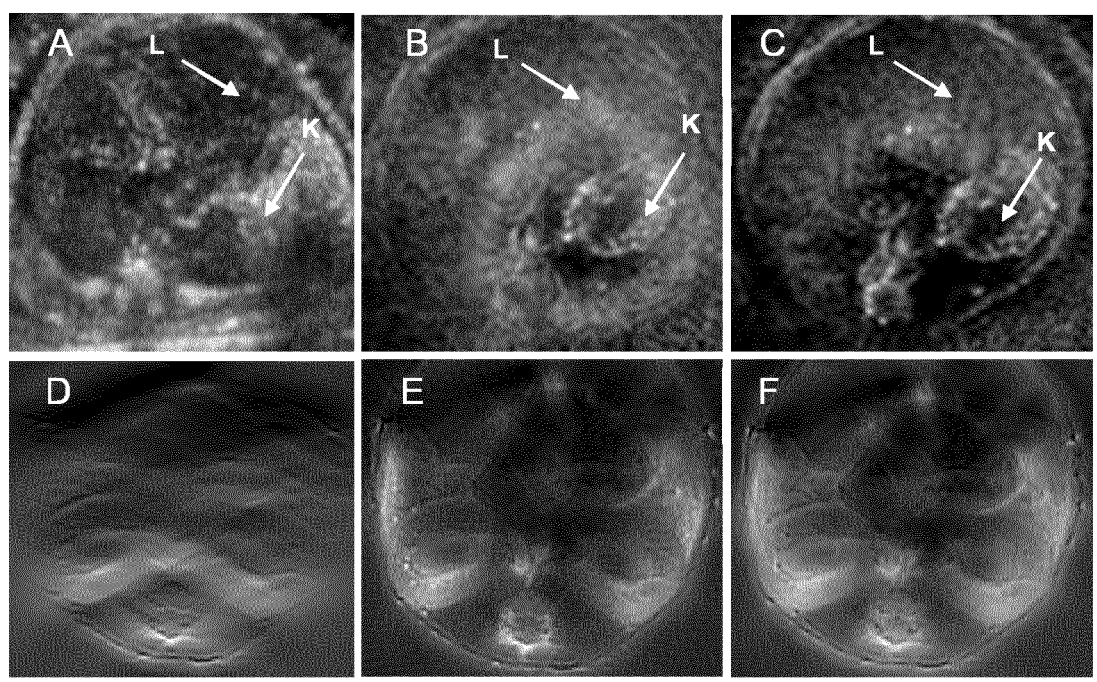
Figure 9:
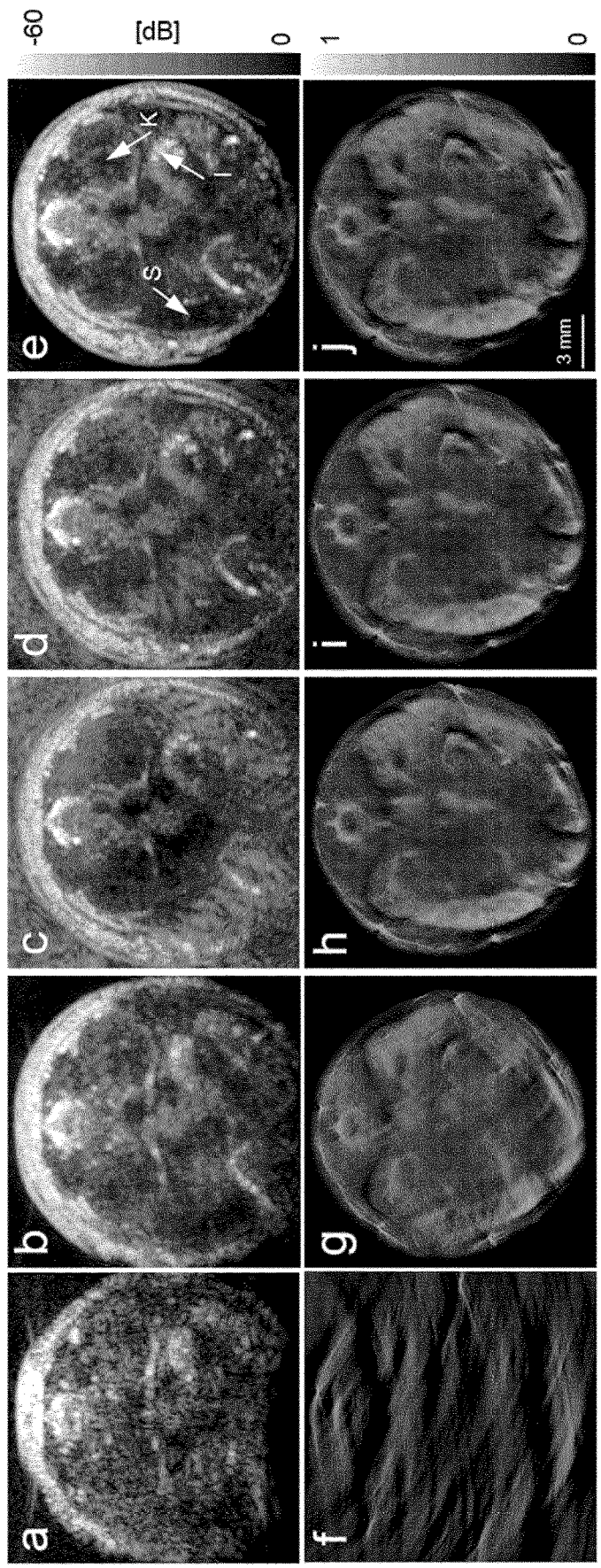

The above and other aspects, alternatives and advantages of the present invention will be elucidated in more detail in the following description of preferred embodiments with reference to the figures showing:

FIG. 1 a) a schematic representation of an example of a device for hybrid optoacoustic and ultrasonographic imaging of an object; b) a cross-sectional representation of a first and second example of a transducer unit;

FIG. 2 a schematic representation of another example of a device for hybrid optoacoustic and ultrasonographic imaging of an object;

FIG. 3 a cross-sectional representation of a third example of a transducer unit;

FIG. 4 a cross-sectional representation of a fourth example of a transducer unit;

FIG. 5 optoacoustic images of a tissue-mimicking phantom (A and B) and a kidney region of a mouse post mortem (D and E) vs. corresponding pulse-echo ultrasound images (C and F) acquired with a common linear array transducer;

FIG. 6 a cross-sectional representation of an arc-shaped transducer geometry (A and B) with angular coverage of 60° and 270° respectively, corresponding optoacoustic images of a tissue-mimicking phantom (E and F) and of a kidney region of a mouse post mortem (G and I);

FIG. 7 a pulse-echo ultrasound image (A) of a cubic agar-based phantom with two cylindrical inclusions acquired with a 128-element concave array (270° angular coverage) with pitch size of 1.47 mm, and pulse-echo ultrasound images (B and C) of the same phantom generated using a common linear array transducer with corresponding pitch size of 1.5 mm and 0.3 mm, respectively;

FIG. 8 reflection-mode ultrasound (A to C) and optoacoustic (D to F) images from a post mortem mouse through the kidneys region; and FIG. 9 further examples of pulse-echo ultrasound images (a to e) and optoacoustic images (f to j) from a mouse in vivo through the kidneys region.

FIG. 1a shows a schematic representation (block diagram) of an example of a device for hybrid optoacoustic (OA) and pulse-echo ultrasonographic (US) imaging of an object 1.

The device comprises an irradiation unit for irradiating the object 1 with electromagnetic radiation, in particular light. In the present example, the irradiation unit comprises a light source 2 which is configured to produce light of varying intensity and/or wavelength. For example, the light source 2 is a pulsed Nd:YAG-pumped optical parameter oscillator (OPO) laser. For example, the laser light source 2 operates at 10 Hz repetition rate, has a tuneable wavelength range of 660-1300 nm, a per-pulse energy of up to 120 mJ and a pulse length of 9 ns.

The light produced by the light source 2 is guided to the object 1 by a light guiding element 3, e.g. an optical fiber bundle. Preferably, at the object-sided end of the light guiding element 3 a light diffusing element (not shown) is provided which is configured to scatter and/or spread the light such that a uniform illumination of the object 1 from multiple angles (indicated by arrows directed towards the object 1) is achieved.

By illuminating the object 1 with transient electromagnetic radiation, acoustic waves, in particular ultrasonic waves, are generated which are detected by a plurality of transducer elements 5 of a transducer unit 4. The transducer elements 4, also referred to as "transducer array", are arranged on at least one concave line and/or at least one concave surface, wherein the concave line or surface has a shape and/or a size and/or is arranged relative to the object 1 such that the transducer elements 4 at least partially surround or encircle the object 1 to be imaged. Preferably, the at least one curved line or surface has a radius of curvature the center of which is located inside the object 1.

Apart from detecting ultrasonic waves generated in the object 1 upon illumination with light in an optoacoustic imaging mode, also referred to as "receive-only mode", at least a part of the transducer elements 5 are also configured to operate in a pulse-echo ultrasonographic imaging mode, also referred to as "transmit-and-receive mode", wherein the transducer elements 5 transmit, i.e. emit, ultrasound waves towards the object 1 and detect ultrasound waves which are reflected and/or transmitted by the object 1.

The transducer unit 4 is connected to a multiplexer unit 10 which is configured to control the transducer elements 5 of the transducer unit 4 to operate in different operation modes, i.e. in the receive-only mode for optoacoustic imaging and/or the transmit-and-receive mode for ultrasonographic imaging and/or a so-called mixed mode, in which ultrasound waves generated in the object 1 upon illumination are received by a first subset (not shown) of the transducer elements 5 and ultrasound waves are emitted by a second subset (not shown) of the transducer elements 5 and ultrasound waves reflected and/or transmitted by the object 1 are received by the second subset of the transducer elements 5, wherein the first subset of transducer elements is different from the second subset of transducer elements. Accordingly, the multiplexer unit 10 allows for a switching between optoacoustic imaging, ultrasonographic imaging and/or combined optoacoustic/ultrasonographic imaging, respectively.

Electric signals corresponding to the optoacoustic waves detected in the receive-only mode are digitized in an optoacoustic data acquisition unit ("OA DAQ"), preferably at a sampling rate of 40 mega samples per second, and the digitized data ("OA Data") are transmitted to a designated computer ("PC") for further processing.

Electric signals corresponding to the ultrasonographic waves detected in the transmit-and-receive mode are transmitted to an ultrasonographic data processing unit ("US Electronics"), which comprises, e.g., a 128-channel beamformer with transmit voltage up to 80 Vpp, central frequency of 5 MHz and receive sampling frequency of 25 MHz. Moreover, the ultrasonographic data processing unit is configured to reconstruct ultrasonographic images based on the received ultrasonographic signals. The reconstructed ultrasonographic Images ("US Images) are transferred as binary raw data files via Ethernet to the computer ("PC").

Preferably, a synchronization between the light source 2, the optoacoustic data acquisition unit ("OA DAQ") and the ultrasonographic data processing unit ("US Electronics") is enabled by means of a control signal ("US Valid") which is generated by the optoacoustic data acquisition unit ("OA DAQ") and transmitted to the ultrasonographic data processing unit ("US Electronics") enabling an ultrasonographic acquisition window.

Figure 1B:
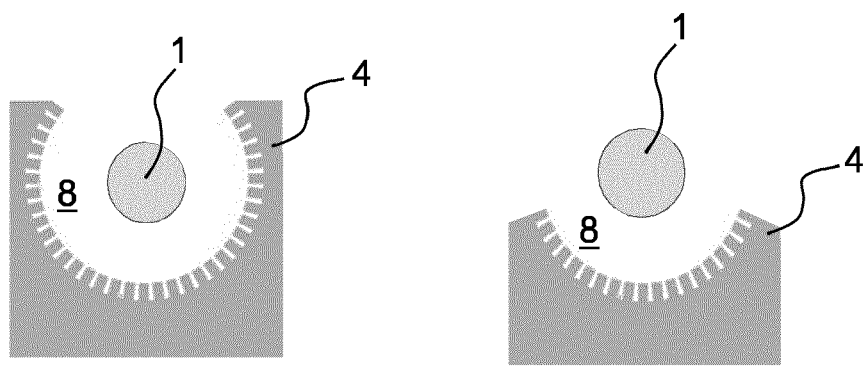

FIG. 1b shows a cross-sectional representation of a first example (left part of figure) and a second example (right part of figure) of a transducer unit 4.

In the first example, the transducer 4 comprises a concave spherical surface on which 128 or 256 transducer elements (not shown) having a center frequency of 5 MHz are provided, wherein the angular coverage of the transducer 4 corresponds to approximately 270°. Preferably, the nominal transmit-receive bandwidth corresponds to approximately 60%, and the radius of curvature of the spherical surface corresponds to approximately 40 mm. Preferably, the pitch size of the individual transducer elements for the 128- and 256-element arrays is 1.47 mm and 0.74 mm, respectively.

In the second example, the transducer 4, which is particularly suitable for handheld use, comprises a concave spherical surface on which 128 or 256 transducer elements (not shown) having center frequencies of 8 MHz and 4 MHz and an angular coverage of approximately 135° are provided. Preferably, the radius of curvature of the spherical surface is also approximately 40 mm. Preferably, 128 transducer elements with 8 MHz central frequency or 256 elements with 4 MHz central frequency are provided having a pitch size of 0.74 mm or 0.37 mm, respectively.

FIG. 2 shows a schematic representation of another example of a device for hybrid optoacoustic and pulse-echo ultrasonographic imaging of an object 1. Instead of providing separate acquisition electronics for optoacoustic and ultrasound reflection and/or transmission tomography (see "OA DAQ" and "US Electronics" in FIG. 1a), the device preferably comprises integrated excitation/detection electronics 11 comprising an ultrasound pulser 12 configured to generate pulses which are fed to the transducer elements 5, an AD conversion unit 13 configured to convert analogue signals received from the transducer elements 5 into corresponding digital signals, an acquisition control unit 14 configured to control the acquisition of optoacoustic and ultrasonographic images, and a frontend 15 configured to execute one or more of the following tasks:
  switching between ultrasound pulser 12 and AD conversion unit 13,
  providing optimized input impedance for different acquisition modes (i.e. OA or US imaging mode),
  pre-amplification, which is optionally adjustable for different acquisition modes (i.e. OA or US imaging mode),
  protection of AD conversion unit 13 from high voltages generated by pulser 12,
  multiplexing a subset of transducer element 5 channels to a subset of channels of the pulser 12 and/or a subset of channels of the AD conversion unit 13.

Optionally, the integrated electronics 11 may be also configured to execute signal preprocessing, filtering or image generation.

Besides, the elucidations set forth above with reference to the example shown in FIG. 1a accordingly apply to the example shown in FIG. 2. According to a preferred embodiment, multitude sizes of the transducer elements are provided. While it is beneficial for optoacoustic imaging to maximize angular coverage, a small pitch of the transducer elements is essential for active ultrasound imaging. These requirements put together would require a high number of channels that need to be sampled at the same time, increasing costs of both electronics and detector. Instead, it is preferred to provide an optimized transducer unit that has transducer elements with different size and/or pitch of the transducer elements, wherein ultrasound imaging is performed with a subset of smaller transducer elements, whilst a high angular coverage is realized with larger transducer elements. Optoacoustic imaging can be performed with all elements, i.e. smaller and larger elements, while ultrasound imaging is restricted to the small elements.

FIG. 3 shows a cross-sectional representation of a third example of an accordingly designed transducer unit 4, where first transducer elements 6 are optimized for ultrasound imaging and second transducer elements 7 are designed to enlarge the angular coverage for improved optoacoustic imaging. Preferably, the size and/or pitch of the first transducer elements 6 is smaller than the size and/or pitch of the second transducer elements 7.

In the present example, the first and second transducer elements 6 and 7 are provided on a concave spherical or cylindrical surface or on a concave line having a radius r of curvature of approximately 6 cm. Preferably, 128 first transducer elements 6 are provided on a first surface section located around the bottom of the concave surface or line. Preferably, the pitch of the first transducer elements 6 is approximately 0.37 mm. Preferably, two second surface sections are provided adjacent to the first surface section, wherein on each of the second surface sections 64 second transducer elements 7 are provided. Preferably, the pitch of the second transducer elements 7 is approximately 1.07 mm.

The center of curvature of the first surface section and the second surface sections defines the focus of the first and second transducer elements 6 and 7, respectively. In the given example, the focus of the first transducer elements 6 on the first surface section and the second transducer elements 7 on the second surface sections coincide in one common focus point F.

Alternatively, a multitude of foci of the first and second transducer elements 6 and 7 may be provided, wherein the position of the foci of the first and second transducer elements 6 and 7 is optimized for ultrasound or optoacoustic imaging, respectively. While in the prior art transducer arrays are typically formed from a single piece of piezo-composite, the transducer unit 4 preferably comprises transducer element arrays which are formed from multiple pieces, which can have different size and/or shape and/or orientation and thus different foci.

This is illustrated in FIG. 4, which shows a cross-sectional representation of a fourth example of an accordingly designed transducer unit 4. In the present example, a first focus F1 of the first transducer elements 6 provided on the first surface section is different from two second foci F2 of the second transducer elements 7 provided on each of the second surface sections. This can be achieved, for example, by tilting the second surface sections, starting from the position shown in FIG. 3, by a tilt angle of approximately 2 to 20° with respect to the first surface section. In this way, the optoacoustic field of view is extended by providing a different elevation of the foci F2 of the second transducer elements 7 provided on the second surface sections versus the first focus F1 of the first transducer elements 6 provided on the first surface section. As a result, compared to the example given in FIG. 3, the first focus F1 of the first transducer elements 6 can be focused deeper into the object to enable deeper ultrasound imaging, since that is less obstructed by light absorption in deep tissues.

Preferably, in order to maintain a sufficient distance to the object 1, e.g. a patient, to allow homogeneous illumination, a couplant compartment 8 (see FIGS. 1 to 4) is provided that is preferably designed to allow coupling of the acoustic waves to the transducer array 4. Preferably, the couplant compartment 8 formed by the concave surface of the transducer unit 4. Preferably, a good couplant in terms of impedance matching is water, which implies that the compartment 8, in order to avoid leakage, has to be sealed by applying a membrane (not shown) to the front face of the transducer unit 4. This also applies for couplant materials that may not come into direct contact with the object, e.g. the skin of a patient, for toxicity or durability reasons.

Preferably, the membrane has an optical as well as acoustical transmission rate of more than 80% (corresponding to low optical and acoustical attenuation). Preferably, aforementioned transmission rates are maintained over the whole range of incident angles from 90° (orthogonal to the membrane) to 0° (parallel to the membrane). In this way it is ensured that the transducer elements 5 to 7 detect a high signal, because light and ultrasound waves are well transmitted through the membrane. In addition, it needs to be stable enough to safely separate the coupling compartment from the outside and withstand common cleaning/disinfection agents and mechanical stress. Depending on the couplant used, the membrane needs to have a sufficient high barrier effect on the contents of the couplant (e.g. water vapor barrier for water based couplant). Suitable base materials are for example (but not restricted to) PTFE, PCTFE, PE, PET, PVC, PVDC and COC. Composites or bonded layers of these materials can be beneficial to combine advantageous properties of different materials (e.g. high chemical stability of PTFE with welding properties of PE). Preferably, the thickness of the membrane is in the range of 5 µm to 500 µm, but not restricted to.

A straight membrane provided at the front end of the transducer unit 4 would reflect acoustic waves, which are generated by the transducer elements either through absorption of stray light in the optoacoustic imaging mode or through emitting ultrasound waves in the ultrasound imaging mode, wherein the reflected wave would hit the transducer elements and create artifacts that obscure the image and limit imaging depth. In order to solve this problem, the membrane is preferably tilted such that ultrasound waves are reflected at the membrane at an angle where the reflected waves do not hit the transducer elements. Alternatively or additionally, the membrane is provided with a curved (e.g. convex or concave) surface that diffracts a reflected wave to not hit the transducer elements.

It is further preferred that the transducer elements are coated with a reflective layer (e.g. gold, silver) which is configured to reflect light, which is reflected by the tissue upon irradiation with light, back to the tissue. In this way the problem is solved that stray light that is reflected on both the membrane and the object boundary (e.g. skin) hits the transducer elements and generates an optoacoustic wave which, upon reflection inside the couplant compartment 8 or at the object interface, can cause artifacts.

Governing Principles of Pulse-Echo Ultrasound Imaging

Ultrasound uses high-frequency acoustic waves transmitted into the imaged tissue and subsequently received by the same ultrasonic transducer. Travel time of the sound wave between the emitted pulse and the returned echo allows calculating the distance to the reflecting interface or point scatterer. Thus, the basic contrast in ultrasound imaging is tissue reflectivity on a pixel-by-pixel basis.

Typically, linear array geometry is used for two-dimensional (cross-sectional) ultrasonography. It usually consists of 128 or 256 regularly spaced transducer elements separated by narrow gaps. In order to achieve cross-sectional imaging capability, the array is usually focused in the imaging plane by means of a cylindrical acoustic lens. When operated as a phased array system, ultrasonic arrays are able to form images employing both steering and focusing the beam in arbitrary direction in the imaged plane by applying suitable time delays on the driving input signals to the array elements. Beamforming at reception can be accomplished analogously to the transmission process with help of delay-and-sum circuitry or digital beamforming. By inducing proper time delays in each channel it is possible to align received echoes before their coherent summation. Under the paraxial approximation, the beam pattern $H(\theta)$ can be expressed as a function of the angle $\theta$ from the center axis of the array to the source point in the imaged plane (x, z), which in the far-field is given by:

$$|H(\theta)| \propto \left| \frac{\sin\left(\frac{N\pi\sin(\theta)d}{\lambda}\right)}{\sin\left(\frac{\pi\sin(\theta)d}{\lambda}\right)} \right|$$

where $\lambda$ is the acoustic wavelength, N is the number of array elements, and d is the distance between the centers of two adjacent elements (pitch size). In order to optimally confine the energy in the main beam of the array and reduce side (grating) lobes, the spatial sampling theorem criterion has to be fulfilled, that is, the pitch size should be ideally less than half the wavelength. If strong scatterers are present in the grating lobes of an undersampled array, they result in ghost responses in the beamformed image, which severely limits contrast in the images. The sidelobe levels can be dealt with by performing a smooth apodization of the aperture by applying windowing functions. On the other hand, the array pitch does not influence the main beam width or the amplitude of the sidelobes. According to the Rayleigh criterion, the ability of ultrasound system to resolve structures in lateral dimension b is defined by the beam directivity, i.e. the distance between the maximum point of the beam pattern and its first zero, which occurs at $$b = \frac{F}{N \cdot d} \cdot \frac{c}{f_0},$$

where $f_0$ is the center frequency of the transducer elements, F is the focal depth and c denotes speed of sound in medium. It can be seen that the beam width in the focal zone is inversely proportional to the transducer aperture size. This suggests making the aperture as large as possible, which in turn imposes limitations on the minimal achievable pitch size.

Since ultrasound imaging uses the pulse-echo method, its axial resolution along the ultrasound propagation direction is determined by the length of the transmitted pulses. For this reason, high frequency system will generally deliver better axial resolution. However, the acoustic pressure field in reflection mode ultrasound is defined by the transducer geometry and does not depend on the size of the scatterers. Centre frequency and the bandwidth of the backscattered and reflected acoustic signals are correspondingly determined by the frequency and duration of the transmitted ultrasound pulse, while the signal amplitude is determined by the acoustic impedance mismatch between tissue boundaries. It is therefore always possible to perform fully dynamic focusing in arbitrary direction with the given spatial resolution and thus produce high-resolution ultrasound images with linear and phased arrays despite their limited tomographic view.

Governing Principles of Optoacoustic Imaging

For light pulse durations much shorter than the temporal resolution of the acoustic detectors, the pressure field $p(\vec{r},t)$ at a specific position $\vec{r}$ and time instant t may be approximated by $$p(\vec{r},t) = \frac{\Gamma}{4\pi c^2} \int d\vec{r}' \frac{1}{|\vec{r}-\vec{r}'|} \frac{\partial H(\vec{r}',t')}{\partial t}\bigg|_{t'=t-|\vec{r}-\vec{r}'|/c'} \quad (3)$$

where $\Gamma = c^2\beta/C_P$ is the dimensionless Grueneisen parameter (c the speed of sound, $\beta$ the isobaric volume expansion coefficient, and $C_P$ the specific heat), $H(\vec{r}',t')$ is distribution of the deposited thermal energy converted per unit volume per unit time, and c is the speed of sound in the medium. For instance, for a delta pulse excitation, the analytical solution for the acoustic pressure, at $\vec{r}_0$ and time t, emitted from a uniformly absorbing spherical source, centered at $\vec{r}_s$ with radius a, can be obtained analytically, i.e.

$$p(\vec{r}_0,t) = A_0 \cdot U(a-|R-ct|)(R-ct)/(2R), \quad (4)$$

where $A_0$ is an amplitude of the initial pressure, U(x) is the step function, c the speed of sound, and $R=|\vec{r}_0-\vec{r}_s|$ is the distance from the center of the sphere.

It can be readily seen that the pressure generated from a spherical absorber will resemble a typical "N-shape" profile, whereas both the magnitude and temporal duration of the signal are proportional to its size. In other words, the optoacoustic signals generated from a typical heterogeneous tissue containing absorbers of different sizes will generally contain frequencies in all spectral bands, including very low frequencies representing the size of the entire illuminated (imaged) region. As a result, the usable frequency range of optoacoustically-generated pressure signals may span an interval between tens of kHz to a few MHz. In order to accurately capture these signals, the ultrasound detectors should ideally possess an ultra-wideband response.

Due to the very broadband frequency content of optoacoustic signals recorded from biological tissues, it becomes then impossible to efficiently focus the detection elements via physical or synthetic aperture techniques in order to obtain accurate spatially resolved information. Moreover, while in ultrasound imaging the focusing can be done in both transmission and detection, only the latter is possible in optoacoustics. Also, the acoustic impedance differences among the different soft tissues may only reach up to 10% in pulse-echo ultrasound, whereas the optical absorption contrast in optoacoustics may reach one or even two orders of magnitude for blood versus other tissues. As a result of both inefficient focusing and high absorption contrast, optoacoustic image formation using phased arrays and other focusing techniques suffers from severe out-of-focus artifacts, impaired contrast, image blurring and overall lack of quantification abilities. Thus, in contrast to pulse-echo ultrasound, correct image reconstruction in optoacoustic imaging is ideally achieved by an unfocused detection of optoacoustic responses from as many tomographic viewing angles as possible around the imaged object. As a result, only the regions effectively enclosed by the detection surface can be reliably reconstructed, while other parts of the image will suffer from limited-view artifacts. In case of linear arrays used in B-mode ultrasonography, the typically available apertures may only provide tomographic view in the range of 40° around the imaged area, making it impossible reconstructing reliable optoacoustic images that correctly represent distribution of the deposited laser energy.

Image Formation

Further preferred aspects regarding the formation of ultrasonographic and optoacoustic images are presented in the following.

For generation of pulse-echo ultrasonographic images from the detected ultrasound waves, a synthetic aperture technique is preferably used. In contrast to conventional "line-by-line" beamforming, the synthetic transmit aperture method implies sequential transmission of pulses from each channel while all transducer elements receive the echo signals. In this way, an unfocused rather than directive ultrasound transmit beam is produced, thus all pixels are uniformly illuminated by the ultrasound wave.

The incoming signals are digitized by an analog-to-digital converter and stored for further processing. Preferably, the final receive transmit beam is synthesized by applying coherent summation across different signals generated as a result of different transmission events. By computing geometric distances from transmit channel to the focal point and back to the receiving channel, the "round-trip" time delays can be incorporated, thus, two-way dynamic focusing is accomplished, both in transmit and receive modes.

The signals are pre-amplified with a gain of 15.5 dB and time-gain-compensation varying from −45 to 0 dB as a function of depth, post-amplified with a gain of 24 dB, and subsequently digitized by a 12-bit analog-to-digital convertor.

The sampled ultrasound echoes are then sent to a computer (PC) for further signal processing. Those include baseband demodulation, beamforming using synthetic aperture, and envelope detection, which results in a sub-image corresponding to a specific sub-aperture with an optimal size.

Preferably, in order to reduce speckle noise and increase the contrast resolution, a spatial compounding technique is subsequently applied across different sub-images corresponding to different sub-apertures. The method implies scanning the same region from multiple viewing angles and incoherently summing up the resulting sub-images to form the final composite image. An overlap between sub-apertures preferably constitutes ¾ times the individual sub-aperture size. Spatial compounding can provide higher level of artifact reduction and speckle noise suppression.

Finally, logarithmic compression is applied to the compounded images and the latter are then displayed with proper gray-level mapping.

For optoacoustic image reconstruction, the detected pressure signals are first processed with a bandpass filter with lower 0.1 MHz and upper 7.5 MHz cutoff frequency in order to reject low frequency offsets and reduce noise. A semi-analytical model-based inverse algorithm is then employed in order to reconstruct the optoacoustic images. In general, the algorithm sets the goal to find an approximation x̂ of unknown image x by minimizing the sum of squared differences between signals theoretically predicted by model A and the pressure signals p actually detected by the ultrasound array. Optical absorption distribution in a matrix form is thus calculated via $$\hat{x}=\mathrm{argmin}_x \|Ax-p\|,$$

where A is the linear operator (or model matrix) mapping the optical absorption to the detected pressure variations.

In the following, optoacoustic and ultrasonographic images obtained with the device and method according to aspects of the invention are shown in comparison with images obtained with conventional devices or methods.

FIG. 5 shows optoacoustic images of a tissue-mimicking phantom reconstructed from signals bandpass-filtered in the frequency range between (A) 0.1 MHz and 7.5 MHz and (B) 1 MHz and 7.5 MHz. The signals were detected by an array with 270° angular coverage; (C) shows a pulse-echo ultrasound image of the same phantom acquired with a common linear array transducer. (D), (E) and (F) show corresponding images recorded from the kidney region of a mouse ex-vivo. Apparently, while images (A) and (D) correctly represent the distribution of the absorbed light energy, images (B), (C), (E) and (F) mainly visualize boundaries of absorbing structures without enabling an extraction of quantitative data from these images.

FIG. 6 demonstrates typical limited-view artifacts in optoacoustic tomographic imaging. Parts (A) and (B) of the figure shows an arc-shaped transducer geometry with angular coverage of 60° and 270° respectively; (E) and (F) show corresponding optoacoustic images of a tissue-mimicking phantom generated using the concave array transducer with limited angular coverage of 60° and an array with 270° angular coverage; (G) and (I) show corresponding images acquired from the kidney region of a mouse post mortem. Apparently, limited angular coverage of the field of view causes severe degradation of optoacoustic image quality, which manifests in characteristic horizontal elongation of circular structures, missing boundaries, hindering correct interpretation of images (see E and G), while the reconstruction accuracy is dramatically improved once tomographic coverage is increased from 60° to 270° (see F and I).

FIG. 7 demonstrates the effect of grating lobes artifacts in ultrasound imaging. Part (A) shows a pulse-echo ultrasound image of a cubic agar-based phantom with two cylindrical inclusions acquired with a 128-element concave array (270° angular coverage) with pitch size of 1.47 mm; (B) and (C) show pulse-echo ultrasound images of the same phantom generated using a common linear array transducer with corresponding pitch size of 1.5 mm and 0.3 mm, respectively. Both images (A) and (B) are corrupted having pronounced side-lobe artifacts and increased speckle noise. Replacing the transducer with a low-pitch size ultrasonic array, readily results in improved quality of the image (C).

FIG. 8 shows optoacoustic and reflection-mode ultrasound images from a post mortem mouse through the kidneys region. (A) shows an ultrasound image acquired with a linear 128-element transducer array; (B) and (C) show pulse-echo ultrasonographic images acquired respectively with a 128-element concave array (1.47 mm pitch) and a 256-element concave array (0.74 mm pitch); (E) and (F) show corresponding optoacoustic images acquired with the two aforementioned concave 128- and 256-element arrays; (D) shows a slice acquired with an array segment covering only 60° around the mouse. For the ultrasonographic images acquired with the concave arrays (see B and C) an increased number of transducer elements and thus finer element pitch size results in better resolved imaging with higher contrast. Furthermore, due to the broad tomographic coverage, the concave arrays were able to evenly visualize the reflection contrast around the entire circumference of the mouse while the linear array geometry was only able to partially capture the cross-section of the mouse (see A). On the other hand, image quality for the optoacoustic mode significantly degrades when tomographic data is acquired under limited view geometry, closely resembling conditions attained by the linear array geometry (see D). In distinction to this, superior image quality and contrast is readily achieved when employing arrays with better tomographic coverage (see E and F). However, only small losses in resolution and aliasing artifacts are observed when acquiring the optoacoustic data with a lower number of 128 projections, thus courser pitch size (see E versus F).

FIG. 9 shows further examples of OA and pulse-echo US images from a mouse in vivo through the kidneys region. (a) US image of the mouse acquired with a small segment (~60° angular coverage) of a 512-element array (0.37 mm pitch), closely resembling a linear array geometry. K—kidney; S—spleen; I—intestines; (b) US image of the mouse acquired with a 256-element concave array (0.37 mm pitch) with 135° angular coverage; (c-e) US images of the mouse acquired with a concave array with 270° angular coverage and pitch size of 1.47 mm, 0.74 mm, and 0.37 mm, respectively; (f-j) show the corresponding OA images acquired with the same arrays as for (a-e). The above elucidations given with respect to FIG. 8 apply accordingly.

What is claimed is:

1. A device for hybrid optoacoustic and ultrasonographic imaging of an object, the device comprising:
   an irradiation source configured to irradiate the object with electromagnetic radiation, in particular light,
   a transducer unit comprising a plurality of transducer elements, the transducer elements being configured to emit ultrasound waves impinging on the object and to detect ultrasound waves which are reflected and/or transmitted by the object upon impinging on the object, and to detect ultrasound waves which are generated in the object upon irradiation with the electromagnetic radiation, wherein the transducer elements are arranged along a curved line or a curved surface, and
   a multiplexer configured to control the transducer unit to operate in different operation modes and to switch the transducer unit between the different operation modes, wherein:
   in a first receive-only mode ultrasound waves generated in the object upon irradiation with the electromagnetic radiation are received by the transducer elements,
   in a second transmit-and-receive mode ultrasound waves are emitted by the transducer elements and ultrasound waves reflected and/or transmitted by the object are received by the transducer elements, and
   in a third mixed mode ultrasound waves generated in the object upon irradiation with the electromagnetic radiation are received by a first subset of the transducer elements and ultrasound waves are emitted by a second subset of the transducer elements and ultrasound waves reflected and/or transmitted by the object are received by the second subset of the transducer elements, wherein the first subset of transducer elements is different from the second subset of transducer elements, and wherein the multiplexer comprises a first electronic circuit designed for acquisition of ultrasound data and a second electronic circuit designed for acquisition of optoacoustic data, the first electronic circuit having a first input impedance and the second electronic circuit having a second input impedance, which is different from the first input impedance.

2. The device according to claim 1, wherein the transducer elements are arranged along a concave line or concave surface, respectively, to cover an angular range of between 120° and 300° around the object, which is preferably located in the center of curvature of the concave line or concave surface, respectively.

3. The device according to claim 1, wherein at least one of the following applies:
the curved line or curved surface, respectively, exhibiting a radius of curvature being in the range between 20 mm and 60 mm,
the transducer elements being configured to emit ultrasound waves in a range of frequencies around a central frequency, the central frequency of the transducer elements being between 2 and 8 MHz,
the arrangement of the transducer elements exhibiting a pitch size in the range of between 0.3 mm and 1 mm, or
the transducer elements exhibiting a pitch size in the range of between 0.1 mm and 3 mm.

4. The device according to claim 1, comprising a controller configured to control the transducer elements:
to sequentially emit ultrasound pulses impinging on the object and
to simultaneously detect ultrasound waves which are reflected and/or transmitted by the object upon impinging on the object,
whereby ultrasound pulses are sequentially transmitted from each of the transducer elements, while the ultrasound pulses reflected and/or transmitted by the object are received by all of the transducer elements.

5. The device according to claim 4, the controller being configured to control the transducer elements such that only transducer elements of a subset of the transducer elements sequentially emit ultrasound pulses impinging on the object and simultaneously detect ultrasound waves which are reflected and/or transmitted by the object upon impinging on the object, whereby ultrasound pulses are sequentially transmitted from each of the transducer elements of the subset of the transducer elements, while the ultrasound pulses reflected and/or transmitted by the object are received by all of the transducer elements of the subset of the transducer elements.

6. The device according to claim 1, comprising a controller configured to control:
transducer elements of a first set of the transducer elements to sequentially emit ultrasound pulses impinging on the object, and
transducer elements of a second set of the transducer elements to simultaneously detect ultrasound waves which are reflected and/or transmitted by the object upon impinging on the object, wherein a distance between the transducer elements of the first set of transducer elements is different to a distance between the transducer elements of the second set of transducer elements,
whereby ultrasound pulses are sequentially transmitted from each of the transducer elements of the first set of transducer elements, while the ultrasound pulses reflected and/or transmitted by the object are received by all of the transducer elements of the second set of transducer elements.

7. The device according to claim 1, comprising a processor configured to perform spatial compounding processing, whereby the same region of the object is scanned from multiple view angles and resulting beamformed images from sub-apertures are incoherently summed up to form a final composite image, wherein each sub-aperture comprises a specific view angle formed by a subset of the transducer elements within the plurality of the transducer elements.

8. The device according to claim 7, wherein the sub-apertures overlap partially.

9. The device according to claim 8, wherein the overlap between the sub-apertures amounts to 0.5 to 0.9 times the individual sub-aperture size.

10. The device according to claim 7, the view angles of the sub-apertures being between 60° and 180°.

11. The device according to claim 7, the transducer elements comprising
first transducer elements being designed for emitting ultrasound waves impinging on the object and detecting ultrasound waves which are reflected and/or transmitted by the object upon impinging on the object, the first transducer elements having a first size and a first pitch, and
second transducer elements being designed for detecting ultrasound waves which are generated in the object upon irradiation with electromagnetic radiation, the second transducer elements having a second size and a second pitch,
wherein the first size of the first transducer elements is smaller than the second size of the second transducer elements and/or the first pitch of the first transducer elements is smaller than the second pitch of the second transducer elements.

12. The device according to claim 11, wherein the first transducer elements being further designed for detecting ultrasound waves which are generated in the object upon irradiation with electromagnetic radiation.

13. The device according to claim 11, wherein the first transducer elements are arranged along a curved line or curved surface to cover a first angular range around the object, and the second transducer elements are arranged along a curved line or curved surface to cover a second angular range around the object, wherein the second angular range is larger than the first angular range.

14. The device according to claim 11, wherein the first transducer elements are arranged along a curved line or curved surface to cover a first angular range around the object, and the first transducer elements and the second transducer elements are arranged along a curved line or curved surface to cover a third angular range around the object, wherein the third angular range is larger than the first angular range.

15. The device according to claim 11, the first transducer elements being part of at least one first transducer element array having at least one first focus, and the second transducer elements being part of at least one second transducer element array having at least one second focus, wherein the at least one first focus does not coincide with the at least one second focus.

16. The device according to claim 1, comprising a data acquisition controller configured to enable a data acquisition-based trigger mode to segment ultrasonographic image acquisition, wherein
   a trigger pulse, preferably created by a pulsed irradiation source, signalizes the start of an individual data acquisition, whereby ultrasound waves are emitted by a subset of transducer elements and ultrasound waves reflected and/or transmitted by the object are received by the subset of transducer elements, and
   an ultrasound image is reconstructed after one or more trigger periods, when a pre-defined number of data acquisitions are complete.

17. The device according to claim 1, comprising a processor configured to reconstruct at least one image of the object based on the detected ultrasound waves, the processor being further configured to progressively update the reconstructed image using ultrasound wave signals from the last N acquisitions, wherein N is an integer, according to a first-in-first-out logic, where data from the first of N acquisitions will be the first one discarded from reconstruction of the next image once the new (N+1)-th acquisition is complete.

18. The device according to claim 1, the device being configured to implement a compressed sensing scheme for synthetic aperture (CSSA), wherein a controller is configured to control the transducer elements to
   sequentially emit ultrasound pulses with each transducer element of selected transducer elements of a first sub-aperture,
   subsequently detect ultrasound waves with all selected receive transducer elements of the first sub-aperture,
   sequentially emit ultrasound pulses with each transducer element of selected transducer elements of a second sub-aperture, and
   subsequently detect ultrasound waves with all selected receive transducer elements of the second sub-aperture,
   wherein the first sub-aperture and the second sub-aperture are each a specific view angle formed by a subset of transducer elements within the plurality of the transducer elements, and
   wherein the transmission with the first element of the second sub-aperture is initiated after a short delay to the transmission with the first element of the first sub-aperture, but simultaneously with the detection on all selected elements of the first sub-aperture for the corresponding transmission event.

19. The device according to claim 1, comprising a processor configured to reconstruct at least one image of the object based on an iterative model-based reconstruction for transmission ultrasound computer tomography (TUCT), wherein maps of local variations of speed of sound and/or acoustic attenuation coefficient are recovered based on an expectation maximization (EM) algorithm with regularization terms, preferably including total variation or total generalized variation.

20. The device according to claim 19, the processor being further configured to increase the accuracy of a time-of-flight estimate by
   deconvolution with a system frequency response obtained from a reference measurement in water, and
   applying a moving average filter, preferably having a size of three, in the time dimension to three successive time-of-flight estimates to suppress the variation of time-of-flight estimation.

21. The device according to claim 1, comprising an image enhancer configured to enhance hybrid images by using combined contrast, wherein at least one of the following applies:
   quality, accuracy and/or specificity of multi spectral optoacoustic tomography (MSOT) images is improved by using anatomical features and/or reflectivity contrast delivered by reflection mode ultrasound computed tomography (RUCT) and/or by using information on heterogeneous sound velocity and acoustic attenuation (AA) distribution in tissue delivered by transmission mode ultrasound computed tomography (TUCT),
   quality, accuracy and/or specificity of RUCT/TUCT images is improved by using anatomical features and optical contrast delivered by MSOT images.

22. The device according to claim 1, comprising a processor configured to reconstruct at least one image of the object based on the detected ultrasound waves and based on a priori knowledge of the heterogeneous speed of sound distribution within the imaged object, which has been determined with transmission ultrasound computer tomography (TUCT).

23. The device according to claim 1, comprising a processor configured to reconstruct at least one quantitative optoacoustic image of the object considering light fluence in the object, wherein the light fluence is modelled including the steps:
   a. creating a multi-level mask which encodes each segmented region of an ultrasound image as an unique integer,
   b. assigning each region an initial estimate of absorption ($\mu_a^0$) and scattering coefficients ($\mu_s^0$),
   c. calculating the fluence using a model of the propagation of light,
   d. calculating the objective function as root mean square error between the measured and calculated absorbed energy maps,
   e. running the solver for the unknown absorption ($\mu_a$) and scattering coefficients ($\mu_s$) of each of the segmented regions that minimizes the objective function using a gradient-based minimization scheme.

24. The device according to claim 23, wherein the model of the propagation of light in step c. is based on the diffusion approximation to the radiative transfer equation.

25. The device according to claim 23, wherein the model of the propagation of light in step c. is based on the δ-Eddington approximation to the radiative transfer equation.

26. The device according to claim 1, the transducer unit having a third input impedance, and the first input impedance of the first electronic circuit being matched with the third input impedance of the transducer unit.

27. The device according to claim 1, comprising a coupling compartment, which is formed by the concave surface of the transducer unit and configured to accommodate a couplant, and a membrane configured to separate the couplant compartment from the outside, in particular from the imaged object, wherein at least one of the following applies:
   the membrane has an optical as well as acoustical transmission rate of at least 80%;
   the membrane has thickness between 5 μm and 500 μm;
   the membrane is tilted to avoid incident wave angles of 90°;

the membrane has a curved, e.g. convex or concave, surface that diffracts an incident wave.

28. The device according to claim 1, the transducer elements being coated with a reflective layer configured to reflect light.

29. The device according to claim 28, the transducer elements and/or the reflective layer being arranged and/or configured to reflect light, which has been reflected by the object upon irradiation with light, back to the object.

30. A method for hybrid optoacoustic and ultrasonographic imaging of an object, comprising:
- irradiating the object with electromagnetic radiation, in particular light, by means of an irradiation source,
- detecting ultrasound waves, which are generated in the object upon irradiating the object with the electromagnetic radiation, by means of a plurality of transducer elements,
- emitting the ultrasound waves impinging on the object by means of the transducer elements,
- detecting the ultrasound waves, which are reflected and/or transmitted by the object upon impinging on the object, by means of the transducer elements, wherein the transducer elements are arranged along a curved line or a curved surface,
- controlling the transducer elements to operate in different operation modes and to switch the transducer elements between the different operation modes, by means of a multiplexer, wherein:
  - in a first mode (receive-only mode) receiving, by means of the transducer elements, ultrasound waves generated in the object upon irradiation with the electromagnetic radiation,
  - in a second mode (transmit-and-receive mode) emitting ultrasound waves, by means of the transducer elements, and receiving, by means of the transducer elements, ultrasound waves reflected and/or transmitted by the object, and
  - in a third mode (mixed mode) receiving, by means of a first subset of the transducer elements, ultrasound waves generated in the object upon irradiation with the electromagnetic radiation, emitting, by means of a second subset of the transducer elements, ultrasound waves, and receiving, by means of the second subset of the transducer elements ultrasound waves reflected and/or transmitted by the object, wherein the first subset of transducer elements is different from the second subset of transducer elements, and
- providing the multiplexer comprising a first electronic circuit designed for acquisition of ultrasound data and a second electronic circuit designed for acquisition of optoacoustic data, the first electronic circuit having a first input impedance and the second electronic circuit having a second input impedance, which is different from the first input impedance.

31. The method for hybrid optoacoustic and ultrasonographic imaging of an object of claim 30, further comprising:
- enhancing hybrid images by using combined contrast, wherein at least one of the following applies:
  - quality, accuracy and/or specificity of multispectral optoacoustic tomography (MSOT) images is improved by using anatomical features and/or reflectivity contrast delivered by reflection mode ultrasound computed tomography (RUCT) and/or by using information on heterogeneous sound velocity and acoustic attenuation (AA) distribution in tissue delivered by transmission mode ultrasound computed tomography (TUCT), or
  - quality, accuracy and/or specificity of RUCT/TUCT images is improved by using anatomical features and optical contrast delivered by MSOT images.

32. The method of claim 31, further comprising:
- enabling a manual segmentation of hybrid images into at least two regions based on dual contrast of the images by:
  - selecting regions on RUCT/TUCT and/or optoacoustic images by placing one or more contours on the current image, and
  - smoothing the contours.

33. The method of claim 31, further comprising:
- enabling an automatic segmentation of hybrid images into at least two regions based on dual contrast of the images by:
  a. image pre-processing using filtering in the frequency domain and/or an anisotropic diffusion filter for noise reduction and edge sharpening,
  b. starting contours initialization, which is determined by means of manual segmentation and/or determined automatically,
  c. automated region growing-shrinking, wherein for each pixel for each of the initial contour selecting the inner (inside the contour) and outer (outside the contour) neighboring pixels, adding or excluding the pixels from the segmented region based on a homogeneity criterion,
  d. updating the borders of the segmented region, and
- repeating steps c. to d. until there are no pixels to add or exclude from the region.

* * * * *

UNITED STATES PATENT AND TRADEMARK OFFICE
CERTIFICATE OF CORRECTION

PATENT NO. : 10,881,299 B2
APPLICATION NO. : 15/316681
DATED : January 5, 2021
INVENTOR(S) : Christian Wiest et al.

Page 1 of 1

It is certified that error appears in the above-identified patent and that said Letters Patent is hereby corrected as shown below:

In the Claims

Column 26, Line 9, in Claim 21, the text "multi spectral" should read --multispectral--; Lines 22-23, in Claim 22, the text "and based on a priori knowledge" should read --and based on an a priori knowledge--.

Column 27, Line 44, in Claim 30, the text "the transducer elements ultrasound waves" should read --the transducer elements, ultrasound waves--.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*